(12) United States Patent
Norcross

(10) Patent No.: US 6,992,083 B2
(45) Date of Patent: Jan. 31, 2006

(54) BENZOXAZOL DERIVATIVES

(75) Inventor: Roger David Norcross, Rheinfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/755,105

(22) Filed: Jan. 9, 2004

(65) Prior Publication Data
US 2004/0152702 A1 Aug. 5, 2004

(30) Foreign Application Priority Data
Jan. 13, 2003 (EP) .................. 03000558

(51) Int. Cl.
C07D 263/58 (2006.01)
C07D 265/30 (2006.01)
A61K 31/421 (2006.01)
A61K 31/423 (2006.01)

(52) U.S. Cl. .................. 514/233.8; 514/338; 514/377; 514/422; 544/138; 546/269.1; 548/222; 548/518; 549/414

(58) Field of Classification Search ................ 514/377, 514/338, 233.8, 422; 548/222, 518; 546/269.1; 544/138; 549/414
See application file for complete search history.

(56) References Cited

U.S. PATENT DOCUMENTS 6,521,754 B2 * 2/2003 Alanine et al. ............. 544/129
6,734,179 B2 * 5/2004 Flohr et al. ............... 514/233.8

FOREIGN PATENT DOCUMENTS

WO        WO 01/97786 A    12/2001

OTHER PUBLICATIONS

Poulsen, S. A. et al., Bioorganic & Medicinal Chemistry, 6, (1998), pp. 619-641.
Müller, C. E. et al., Bioorganic & Medicinal Chemistry, 6, (1998), pp. 707-719.
Kim, Y. C. et al., J. Med. Chem., (1998), 41, pp. 2835-2845.
Li, A. H. et al., J. Med. Chem., (1998), 41, pp. 3186-3201.
Baraldi, P. G. et al. J. Med. Chem. (1998), 41, pp. 2126-2133.
Li, A. H., et al., J. Med. Chem. (1999), 42, pp. 706-721.
Baraldi, P. G. et al., J. Med. Chem., (1996), 39, pp. 1164-1171.
Colotta, V. et al., Arch. Pharm. Med. Chem., 332, pp. 39-41 (1999).
Auchampach, J. A. et al., Am. J. Physiol., 276, H1113-1116 (1999).
Naunyn-Schmiedeberg, Arch. Pharmacol. 362, pp. 375-381 (2000).
Dionisotti S. et al., Br. J. Pharmacol. 121, pp. 353-360 (1997).

* cited by examiner

Primary Examiner—Taofiq Solola
Assistant Examiner—Susannah E. Lee
(74) Attorney, Agent, or Firm—George W. Johnston; Patricia S. Rocha-Tramaloni; Kimberly J. Prior

(57) ABSTRACT

The invention relates to compounds of formula

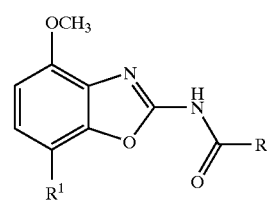

wherein
R is phenyl, unsubstituted or substituted by halogen or
—$CH_2N(CH_3)(CH_2)_nOCH_3$, or
is benzyl,
lower alkyl,
lower alkoxy,
—$(CH_2)_nOCH_3$, or is
pyridin 3 -or 4-yl, unsubstituted or substituted by lower alkyl, halogen, morpholinyl, —$(CH_2)_n$-halogen, —$(CH_2)_nOCH_3$, —$(CH_2)_n$-morpholin-4-yl, or —$(CH_2)_n$- pyrrolidin-1-yl;
$R^1$ is phenyl or unsubstituted or substituted by halogen, tetrahydropyran-4-yl, 3,6-dihydro-2H-pyran-4-yl or morpholin-4-yl;
n is independently from each other 1 or 2;
and to pharmaceutically acceptable salts thereof for the treatment of diseases related to the adenosine $A_{2A}$-receptor.

25 Claims, No Drawings

BENZOXAZOL DERIVATIVES

FIELD OF THE INVENTION

The invention relates to adenosine receptor ligands, methods for their production, and their use for the treatment of central nervous system diseases.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanisms. These mechanisms are dependent on the receptor associated G protein. Each of the adenosine receptor subtype has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system includes the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioural state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonist modulates the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications:
Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H1113–1116, (1999) or
Naunyn Schmied, Arch. Pharmacol. 362, 375–381, (2000).

SUMMARY OF THE INVENTION

One object of the present invention is to provide compounds of formula I per se and their pharmaceutically acceptable salts.

In particular, the present invention provides compounds of the general formula

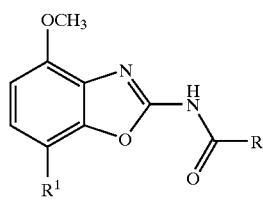

I wherein
R is phenyl, unsubstituted or substituted by halogen or
    —CH$_2$N(CH$_3$)(CH$_2$)$_n$OCH$_3$, or
  is benzyl,
  lower alkyl,
  lower alkoxy,
  —(CH$_2$)$_n$OCH$_3$, or is
  pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl;
R$^1$ is phenyl, unsubstituted or substituted by halogen, tetrahydropyran-4-yl, 3,6-dihydro-2H-pyran-4-yl or morpholin-4-yl;
n are independently 1 or 2;

or a pharmaceutically acceptable salt thereof.

It is another object of the present invention to provide methods for the manufacture of compounds of formula I and their pharmaceutically acceptable salts.

It has surprisingly been found that the compounds of general formula I are adenosine receptor ligands. Specifically, the compounds of the present invention have a good affinity to the A$_{2A}$-receptor and a high selectivity to the A$_1$- and A$_3$ receptors. Therefore, it is another object of the present invention to provide pharmaceutical compositions containing the compounds of the invention. It is yet another object of the present invention to provide methods of using the compounds of formula I in the control or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents for disorders such as coronary artery disease and heart failure. The most preferred indications in accordance with the present invention are those, which base on the A$_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DESCRIPTION OF THE INVENTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" of a compound means salts that are pharmaceutically acceptable, which are generally safe, non-toxic, and neither biologically nor otherwise undesirable, and that possess the desired pharmacological activity of the parent compound. "Pharmaceutically acceptable salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like. It should be understood that pharmaceutically acceptable salts include solvent addition forms (solvates) or crystal forms (polymorphs) of the same salts.

"Therapeutically effective amount" means an amount that is effective to prevent, alleviate, or ameliorate symptoms of disease or prolong the survival of the subject being treated.

The present invention provides compounds of the general formula

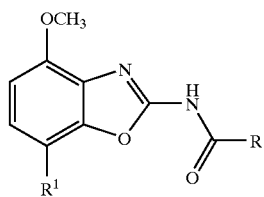

I wherein
R is phenyl, unsubstituted or substituted by halogen or
    —CH$_2$N(CH$_3$)(CH$_2$)$_n$OCH$_3$, or
  is benzyl,
  lower alkyl, lower alkoxy,
—(CH$_2$)$_n$OCH$_3$, or is
pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl;

R$^1$ is phenyl, unsubstituted or substituted by halogen, tetrahydropyran-4-yl, 3,6-dihydro-2H-pyran-4-yl or morpholin-4-yl;

n are independently 1 or 2;

or a pharmaceutically acceptable salt thereof.

In one embodiment, the invention provides compounds wherein R$^1$ is 4-fluor phenyl. For example, this embodiment includes compounds in which R is selected from phenyl, unsubstituted or substituted by halogen or —CH$_2$N(CH$_3$)(CH$_2$)OCH$_3$, and benzyl. Also included are compounds of formula I in which R is selected from lower alkyl, lower alkoxy, and —(CH$_2$)$_n$OCH$_3$, and n is independently from each other 1 or 2. Further included are compounds in which R is pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl.

Preferred compounds of the present application are compounds of formula I, wherein R$^1$ is 4-fluoro phenyl. Such compounds are 2-Chloromethyl-N-[7-(4-fluoro-phenyl)-4-methoxy-benzooxazol-2-yl]-isonicotinamide, N-[7-(4-fluoro-phenyl)-4-methoxy-benzooxazol-2-yl]-2-methyl-isonicotinamide, N-[7-(4-fluoro-phenyl)-4-methoxy-benzooxazol-2-yl]-6-methyl-nicotinamide 4-fluoro-N-[7-(4-fluoro-phenyl)-4-methoxy-benzooxazol-2-yl]-benzamide, N-[7-(4-fluoro-phenyl)-4-methoxy-benzooxazol-2-yl]-2-morpholin-4-yl-isonicotinamide or N-[7-(4-fluoro-phenyl)-4-methoxy-benzooxazol-2-yl]-2-methoxymethyl-isonicotinamide.

In another embodiment, the invention provides compounds wherein R$^1$ is unsubstituted phenyl. For example, this embodiment includes compounds in which R is selected from phenyl, unsubstituted or substituted by halogen or —CH$_2$N(CH$_3$)(CH$_2$)OCH$_3$, and benzyl. Also included are compounds of formula I in which R is selected from lower alkyl, lower alkoxy, and —(CH$_2$)$_n$OCH$_3$, and n is independently from each other 1 or 2. Further included are compounds in which R is pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl.

Further preferred are compounds of formula I, wherein R$^1$ is unsubstituted phenyl, for example the following compounds:

4-Fluoro-N-(4-methoxy-7-phenyl-benzooxazol-2-yl)-benzamide or

4-{[(2-methoxy-ethyl)-methyl-amino]-methyl}-N-(4-methoxy-7-phenyl-benzooxazol-2-yl)-benzamide.

In a further embodiment, the invention provides compounds wherein R$^1$ is tetrahydropyran-4-yl. For example, this embodiment includes compounds in which R is selected from phenyl, unsubstituted or substituted by halogen or —CH$_2$N(CH$_3$)(CH$_2$)OCH$_3$, and benzyl. Also included are compounds of formula I in which R is selected from lower alkyl, lower alkoxy, and —(CH$_2$)$_n$OCH$_3$, and n is independently from each other 1 or 2. Further included are compounds in which R is pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl.

Further preferred are compounds, wherein R$^1$ is tetrahydropyran-4-yl, for example the following compounds:

N-[4-Methoxy-7-(tetrahydro-pyran-4-yl)-benzooxazol-2-yl]-6-methyl-nicotinamide or N-[4-methoxy-7-(tetrahydro-pyran-4-yl)-benzooxazol-2-yl]-2-methyl-isonicotinamide.

The present compounds of formula I and their pharmaceutically acceptable salts can be prepared by methods known in the art, for example, by processes described below, which processes comprise a) reacting a compound of formula

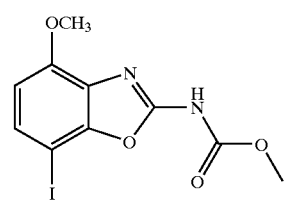

(6)

with a compound of formula

R$^1$SnBu$_3$/cat. Pd(O)  (7) or with a compound of formula

R$^1$B(OH)$_2$/cat. Pd(O)  (10)

to a compound of formula

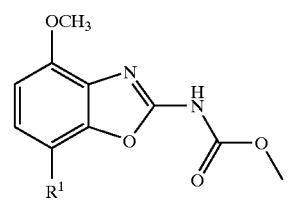

I(8)

wherein R$^1$ is phenyl, unsubstituted or substituted by halogen, or b) reacting a compound of formula

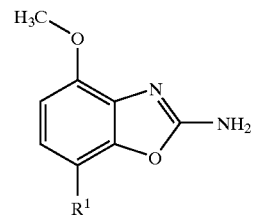

(9)

with a compound of formula

ClC(O)R/base  (11)

or with a compound of formula

HOC(O)R/HATU/base  (12)

to a compound of formula

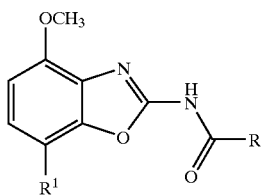

I wherein R¹ is unsubstituted phenyl or substituted by halogen, or c) hydrogenating a compound of formula

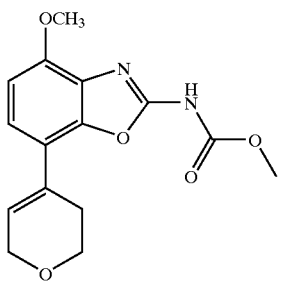

I(15)

with H₂/Pd/C to a compound of formula

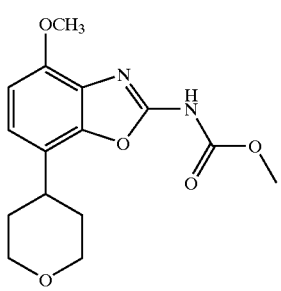

I(16)

or d) reacting a compound of formula

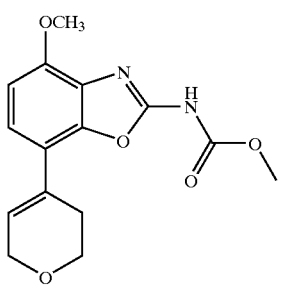

I(15)

with NaOH and then with a compound of formula

ClC(O)R/base (11)

or with a compound of formula

HOC(O)R/HATU/base (12)

to a compound of formula

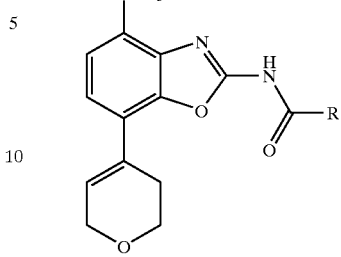

Ia or e) reacting a compound of formula

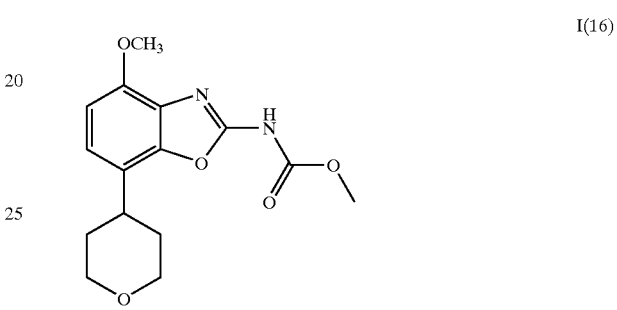

I(16)

with NaOH and then with a compound of formula

ClC(O)R/base (11)

or with a compound of formula

HOC(O)R/HATU/base (12)

to a compound of formula

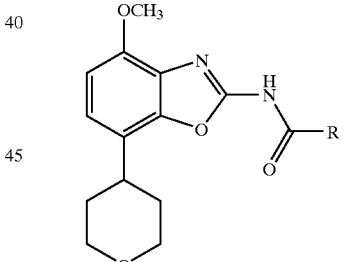

Ib or f) reacting a compound of formula

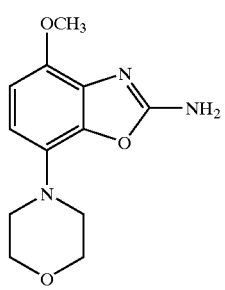

(20)

with a compound of formula

ClC(O)R/base (11)

or with a compound of formula

HOC(O)R/HATU/base (12)

to a compound of formula

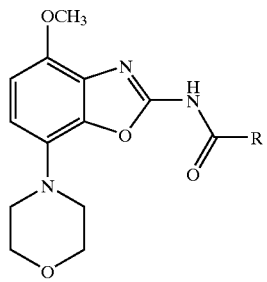

(Ic)

or g) modifying one or more substituents $R^1$ or R within the definitions given above, and if desired, converting the compounds obtained into pharmaceutically acceptable acid addition salts.

The compounds of formula I may be prepared in accordance with the following schemes:

Preparation of Compounds of Formula I where $R^1$ is Phenyl or Halogen-substituted Phenyl One method of preparation of compounds of formula I, where $R^1$ is phenyl or halogen-substituted phenyl, is from an intermediate of formula (5), as shown in scheme II below.

The preparation of the intermediate of formula (5) is shown in reaction scheme I below.

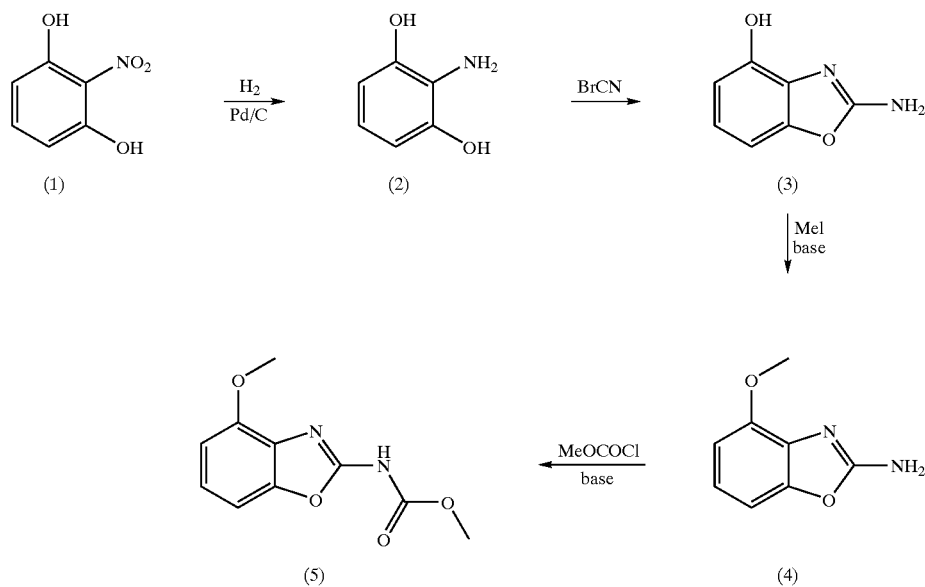

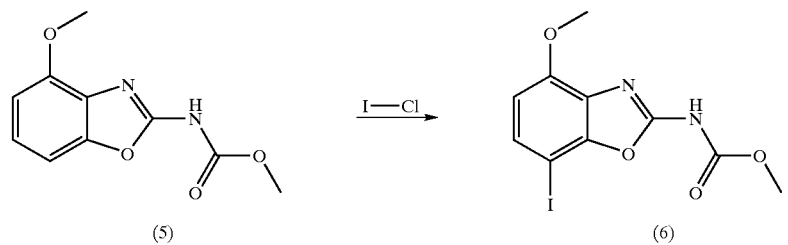

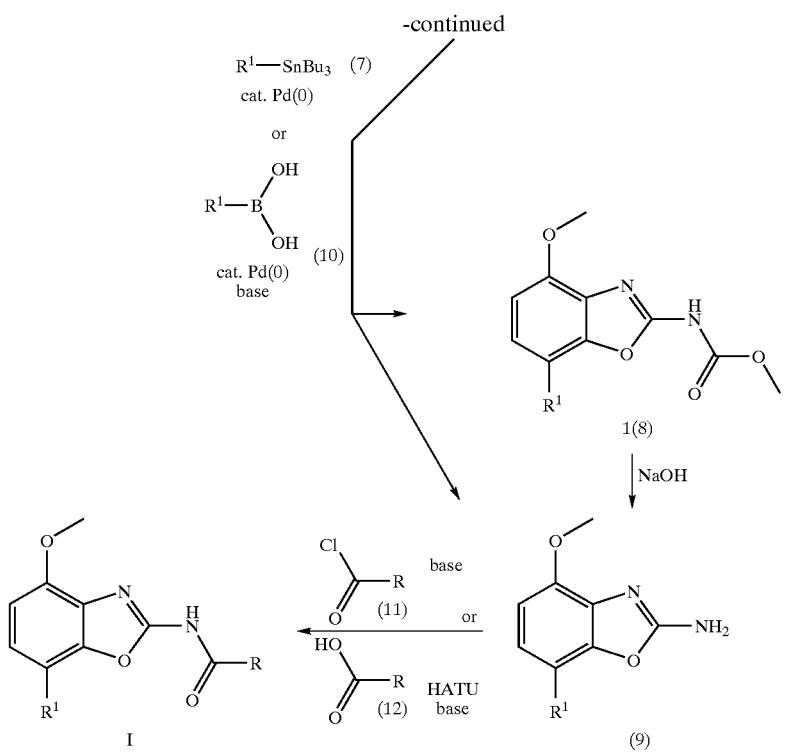

where $R^1$ is phenyl or halogen-substituted phenyl and R' is as defined above.

Preparation of Intermediate of Formula (2)

The starting 2-nitroresorcinol of formula (1) may be obtained commercially, for example from Aldrich, or may be prepared according to methods well known in the art.

The 2-nitroresorcinol of formula (1) is hydrogenated in the presence of a hydrogenation catalyst, preferably 10% palladium on charcoal. This reaction may be carried out in a variety of organic solvents, such as methanol, ethanol, dioxane or tetrahydrofuran, preferably methanol, at room temperature and at a pressure of one atmosphere or above, preferably at one atmosphere, for 2–24 hours, preferably about 18 hours. The product of formula (2), 2-aminoresorcinol, is preferably used in the next step without purification.

Preparation of Intermediate of Formula (3)

The intermediate of formula (2) is reacted with a slight excess of cyanogen bromide in an aqueous solvent mixture, preferably a mixture of a lower alcohol and water, preferably a mixture of methanol and water. The reaction is preferably carried out at room temperature for about 2 hours. The product benzoxazole compound of formula (3) is isolated by conventional means, and preferably purified by means of chromatography or recrystallisation.

Preparation of Intermediate of Formula (4)

One method of preparation of an intermediate of formula (4) is by treatment of the intermediate of formula (3) with a slight excess of a strong base, preferably sodium hydride, in a non-protic solvent, preferably tetrahydrofuran, at an elevated temperature, preferably about 50° C., for about 1 hour; the intermediate compound so-produced is subsequently treated with methyl iodide, preferably with about one equivalent of methyl iodide, at an elevated temperature, preferably about 50° C., for 1–5 hours, preferably about 3 hours. The product of formula (4) is isolated by conventional means, and preferably purified by means of chromatography or recrystallisation.

Preparation of Intermediate of Formula (5)

The intermediate of formula (4) is reacted with a slight excess of methyl chloroformate in an organic solvent, preferably dichloromethane. The reaction is carried out in the presence of an amine base such as pyridine, triethylamine or N-ethyldiisopropylamine, preferably pyridine, at a temperature below room temperature, preferably at 0° C., for 0.25–4 hours. The product of formula (5) is isolated by conventional means, and preferably purified by means of chromatography or recrystallisation.

Preparation of Intermediate of Formula (6)

The intermediate of formula (5) is reacted with a slight excess of an iodinating reagent, preferably iodine monochloride, in an organic solvent, preferably acetic acid. The reaction is carried out in the presence of a weak base, preferably sodium acetate, at room temperature for about 2–30 hours, preferably about 16 hours. The product of formula (6) is isolated by conventional means, and preferably purified by means of chromatography or recrystallisation.

Preparation of Compounds of Formula I(8) and/or Formula (9)

The starting tributylstannane compounds of formula (7) maybe obtained commercially, for example from Fluka, or may be prepared according to methods well known in the art.

The intermediate of formula (6) is reacted with an excess of a tributylstannane compound of formula (7) in an organic solvent, preferably N,N-dimethylformamide, containing a palladium catalyst, preferably tris(dibenzylideneacetone)dipalladium(0), a catalytic amount of a phosphine or arsine ligand, preferably triphenylarsine, and an excess of a copper (I) salt, preferably copper(I) iodide. The reaction is carried out at elevated temperature, preferably about 80° C., for about 2–24 hours, preferably about 16 hours. The product(s) is(are) isolated by conventional means, and preferably purified by means of chromatography or recrystallisation. Depending on parameters such as the reaction temperature and the reaction time the major product of the reaction may in some cases be a compound of formula I(8), in other cases the major product may be a compound of formula (9), or the reaction may deliver a mixture of products of formula I(8) and (9).

Alternative Preparation of Compounds of Formula I(8) and/or Formula (9)

The starting boronic acid compounds of formula (10) may be obtained commercially, for example from Fluka, or may be prepared according to methods well known in the art.

The compounds of formula I(8) or (9) may alternatively be prepared by treating the intermediate of formula (6) with an excess of a boronic acid compound of formula (10). The reaction is carried out in an aqueous solvent, preferably a mixture of water, dioxane and 1,2-diethoxyethane, containing a palladium catalyst, preferably tetrakis (triphenylphosphine)palladium(0), an excess of a lithium salt, preferably lithium chloride, and an inorganic base, preferably sodium carbonate. The reaction is preferably carried out at the reflux temperature of the solvent, preferably about 100° C., for about 2–24 hours, preferably about 16 hours. The product(s) is(are) isolated by conventional means, and preferably purified by means of chromatography or recrystallisation. Depending on parameters such as the reaction temperature and the reaction time the major product of the reaction may in some cases be a compound of formula I(8), in other cases the major product may be a compound of formula (9), or the reaction may deliver a mixture of products of formula I(8) and (9).

Preparation of Intermediates of Formula (9) from Compounds of Formula I(8)

Compounds of formula I(8) may be converted to the corresponding intermediates of formula (9) by reaction with an excess of an aqueous base such as lithium hydroxide, sodium hydroxide or potassium hydroxide, preferably sodium hydroxide. The reaction is carried out in an aqueous solvent, preferably a mixture of water and a miscible organic solvent such as dioxane, tetrahydrofuran or ethylene glycol, preferably ethylene glycol, at an elevated temperature, preferably at the reflux temperature of the solvent, for about 2–16 hours, preferably about 16 hours. The product of formula (9) is isolated by conventional means, and preferably purified by means of chromatography or recrystallisation.

Preparation of Compounds of Formula I where $R^1$ is Phenyl or Halogen-substituted Phenyl One method of preparation of compounds of formula I, where $R^1$ is phenyl or halogen-substituted phenyl, is by treatment of an intermediate of formula (9) with a slight excess of an appropriate acyl chloride of formula (11), which may be commercially available or may be prepared by methods well known in the art. A catalyst such as N,N-dimethyl-4-aminopyridine may also be used. The reaction is carried out in a non-protic organic solvent, preferably a mixture of dichloromethane and tetrahydrofuran, containing a base, preferably N-ethyldiisopropylamine or triethylamine, at a temperature between room temperature and the reflux temperature of the solvent for 2–24 hours, preferably 16 hours. The product of formula I, where $R^1$ is phenyl or halogen-substituted phenyl, is isolated by conventional means, and preferably purified by means of chromatography or recrystallisation.

Alternative Preparation of Compounds of Formula I where $R^1$ is Phenyl or Halogen-substituted Phenyl An alternative method of preparation of compounds of formula I, where $R^1$ is phenyl or halogen-substituted phenyl, involves treatment of an appropriate carboxylic acid of formula (12) with a stoichiometric equivalent of a peptide-coupling reagent, preferably O-(7-azabenzotriazol-1-yl)-N,N,N',N'-tetramethyluronium hexafluorophosphate (HATU), in an ethereal solvent, preferably tetrahydrofuran, containing a base, preferably N-ethyldiisopropylamine, at room temperature for 30–90 minutes, preferably 1 hour. This mixture is then treated with an intermediates of formula (9) in a solvent mixture, preferably a mixture of tetrahydrofuran, dioxane and N,N-dimethylformamide, at room temperature for 16–24 hours, preferably 16 hours. The product of formula I, where $R^1$ is phenyl or halogen-substituted phenyl, is isolated by conventional means, and preferably purified by means of chromatography or recrystallisation.

Preparation of compounds of formula I where $R^1$ is 3,6-dihydro-2H-pyran-4-yl or tetrahydropyran-4-yl One method of preparation of compounds of formula I, where $R^1$ is 3,6-dihydro-2H-pyran-4-yl or tetrahydropyran-4-yl, is from an intermediate of formula (6), as shown in Scheme 3 below.

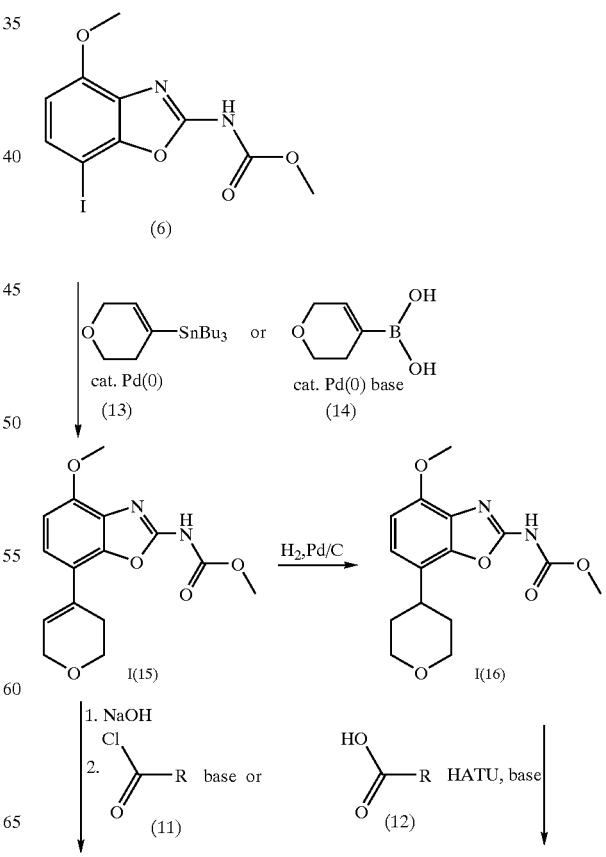

-continued

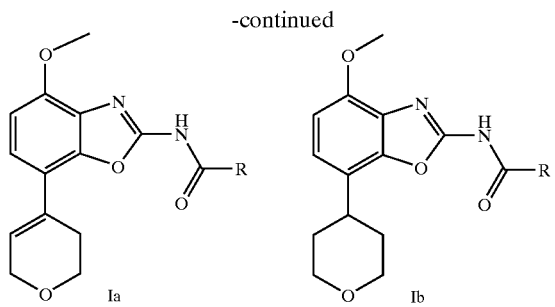

where R is as defined above.

Preparation of Compounds of Formula I(15)

The starting tributylstannane compound of formula (13) maybe prepared according to methods well known in the art.

The intermediate of formula (6) is reacted with an excess of the tributylstannane compound of formula (13) in an organic solvent, preferably dioxane, containing a palladium catalyst, preferably dis(dibenzylideneacetone)palladium(0), and a catalytic amount of a phosphine or arsine ligand, preferably tri(2-furyl)phosphine. The reaction is carried out at elevated temperature, preferably about 100° C., for about 2–24 hours, preferably about 16 hours. The product of formula I(15) is isolated by conventional means, and preferably purified by means of chromatography or recrystallisation.

Alternative Preparation of Compounds of Formula I(15)

The starting boronic acid compound of formula (14) may be prepared according to methods well known in the art.

The compounds of formula I(15) may alternatively be prepared by treating the intermediate of formula (6) with an excess of the boronic acid compound of formula (14). The reaction is carried out in an aqueous solvent, preferably a mixture of water, dioxane and 1,2-diethoxyethane, containing a palladium catalyst, preferably tetrakis (triphenylphosphine)palladium(0), and an inorganic base, preferably sodium carbonate. The reaction is preferably carried out at the reflux temperature of the solvent, preferably about 100° C., for about 2–24 hours, preferably about 16 hours. The product of formula I(15) is isolated by conventional means, and preferably purified by means of chromatography or recrystallisation.

Preparation of Compounds of Formula I(16)

The compounds of formula I(15) maybe converted to the compounds of formula I(16) by hydrogenation in the presence of a hydrogenation catalyst, preferably 10% palladium on charcoal. This reaction may be carried out in a variety of organic solvents, such as methanol, ethanol, dioxane, tetrahydrofuran or dichloromethane, preferably a mixture of methanol and dichloromethane, at room temperature and at a pressure of one atmosphere or above, preferably at one atmosphere, for 2–24 hours, preferably about 18 hours. The product of formula I(16) is isolated by conventional means, and preferably purified by means of chromatography or recrystallisation.

Preparation of compounds of formula I where $R^1$ is 3,6-dihydro-2H-pyran-4-yl (Ia)

Compounds of formula I, where $R^1$ is 3,6-dihydro-2H-pyran-4-yl, may be prepared from the compounds of formula I(15) by methods exactly analogous to those described above for the preparation of compounds of formula I from intermediates of formula (8). The product of formula I, where $R^1$ is 3,6-dihydro-2H-pyran-4-yl, is isolated by conventional means, and preferably purified by means of chromatography or recrystallisation.

Preparation of Compounds of Formula I where $R^1$ is Tetrahydropyran-4-yl (Ib)

Compounds of formula I, where $R^1$ is tetrahydropyran-4-yl may be prepared from the compounds of formula I(16) by methods exactly analogous to those described above for the preparation of compounds of formula I from intermediates of formula (8). The product of formula I, where $R^1$ is tetrahydropyran-4-yl, is isolated by conventional means, and preferably purified by means of chromatography or recrystallisation.

Preparation of Compounds of Formula I where $R^1$ is Morpholin-4-yl

One method of preparation of compounds of formula I, where $R^1$ is morpholin-4-yl, is from an intermediate of formula (5), as shown in Scheme 4 below.

Scheme 4

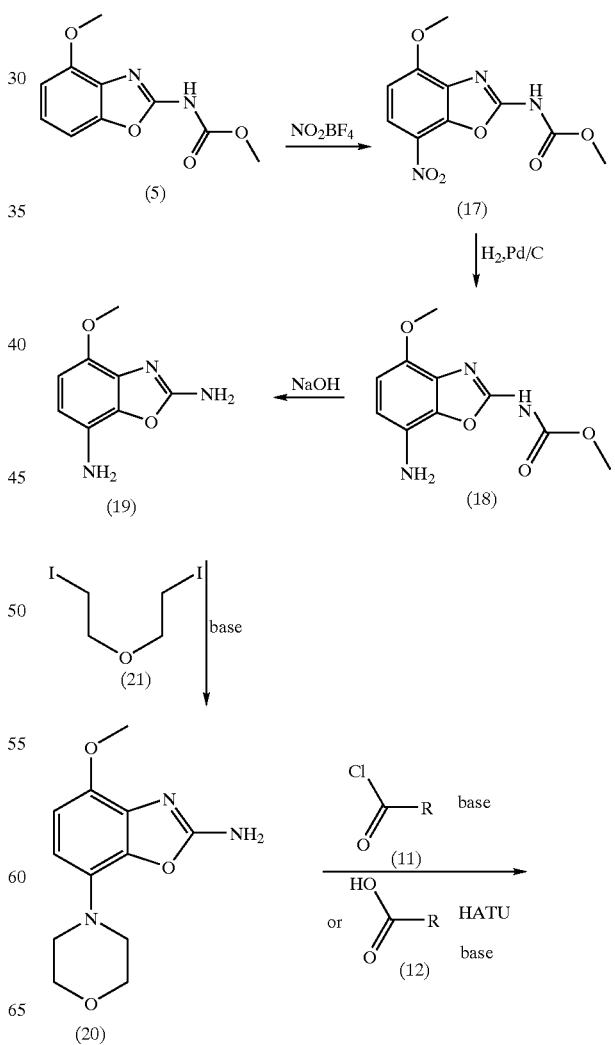

-continued

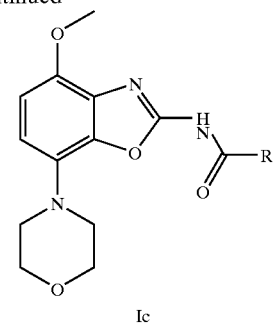

Ic where R is as defined above.

Preparation of Intermediate of Formula (17)

The intermediate of formula (5) is reacted with a nitrating agent, preferably nitronium tetrafluoroborate, in a polar organic solvent, preferably nitromethane. The reaction is carried out at a temperature between 0° C. and room temperature for about 2–24 hours, preferably about 18 hours. The product of formula (17) is isolated by conventional means, and preferably purified by means of chromatography or recrystallisation.

Preparation of Intermediate of Formula (18)

The intermediate of formula (17) maybe converted to the intermediate of formula (18) by hydrogenation in the presence of a hydrogenation catalyst, preferably 10% palladium on charcoal. This reaction may be carried out in a variety of organic solvents, such as methanol, ethanol, dioxane, tetrahydrofuran or dichloromethane, preferably a mixture of methanol and dichoromethane, at room temperature and at a pressure of one atmosphere or above, preferably at one atmosphere, for 2–24 hours, preferably about 18 hours. The product of formula (18) is isolated by conventional means, and preferably purified by means of chromatography or recrystallisation.

Preparation of Intermediate of Formula (19)

The intermediate of formula (18) may be converted to the intermediate of formula (19) by reaction with an excess of an aqueous base such as lithium hydroxide, sodium hydroxide or potassium hydroxide, preferably sodium hydroxide. The reaction is carried out in an aqueous solvent, preferably a mixture of water and a miscible organic solvent such dioxane, tetrahydrofuran or ethylene glycol, preferably a mixture of water, dioxane and ethylene glycol, at an elevated temperature, preferably at the reflux temperature of the solvent, for about 2–16 hours, preferably about 4 hours. The product of formula (19) is isolated by conventional means, and preferably purified by means of chromatography or recrystallisation.

Preparation of Intermediate of Formula (20)

The intermediate of formula (19) is reacted with the alkyl di-iodide compound of formula (21), which maybe prepared according to methods well known in the art, in an organic solvent, preferably N,N-dimethylformamide, containing a base, preferably potassium carbonate. The reaction is carried out at a temperature between room temperature and the reflux temperature of the solvent, preferably at about 60° C., for about 1–48 hours, preferably about 48 hours. The product of formula (20) is isolated by conventional means, and preferably purified by means of chromatography or recrystallisation.

Preparation of Compounds of Formula Ic ($R^1$ is Morpholin-4-yl)

Compounds of formula I, where $R^1$ is morpholin-4-yl, may be prepared from the intermediate of formula (20) by methods exactly analogous to those described above for the preparation of compounds of formula I from intermediates of formula (9). The product of formula I, where $R^1$ is morpholin-4-yl, is isolated by conventional means, and preferably purified by means of chromatography or recrystallisation.

Conversion of Compounds of Formula I to other Compounds of Formula I Bearing a Modified R Substituent In cases where the compound of formula I contains an R substituent bearing a chemically reactive functional group, for instance when R contains benzylic halide functionality or 2-halo-pyridyl functionality, the compound of formula I may be converted to another compound of formula I having a modified R substituent, by reactions involving the reactive functionality contained in the original R substituent. Such transformations may be carried out according to methods well known in the art and specific examples may be had from a number of the examples provided below. For instance, compounds of formula I containing R substituents bearing benzylic halide functionality or 2-halo-pyridyl functionality may be reacted with nucleophilic alcohol or amine reagents to afford compounds of formula I containing R substituents bearing, respectively, benzylic ether or benzylic amine functional groups, or pyridyl-2-yl-ether or pyridyl-2-yl-amino functional groups.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands ($A_{2A}$). Furthermore, it has been shown that the preferred compounds of formula I have a good selectivity to the $A_1$ receptor in the range of 26 to 650.

The compounds were investigated in accordance with the tests given hereinafter.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The preferred compounds show a pKi>7.5. In the following table the affinity to the A2a receptor and its selectivity to the $A_1$ receptor is shown for these compounds.

| Example | hA2a pKi | selectivity to hA1 |
|---|---|---|
| 1 | 7.92 | 26 |
| 2 | 7.65 | 137 |
| 5 | 7.66 | 140 |
| 9 | 7.66 | 351 |
| 13 | 7.64 | 227 |
| 14 | 7.80 | 134 |
| 17 | 7.89 | 242 |
| 18 | 8.19 | 120 |
| 20 | 8.07 | 650 |
| 21 | 7.52 | 96 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Therefore, the invention also provides pharmaceutical compositions containing a compound of the invention and a pharmaceutically acceptable carrier. The compositions of the invention can also contain one or more other therapeutically valuable substance and be formulated into a galenical administration form together with the one or more pharmaceutically acceptable carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardioprotective agents and for the production of corresponding medicaments.

The most preferred indications in accordance with the present invention are those, which include disorders of the central nervous system, for example the treatment or prevention of certain depressive disorders, neuroprotection and Parkinson's disease.

Therefore, the present invention provides a method for treating Parkinson's disease which comprises administering to an individual a therapeutically effective amount of a compound of formula I. The invention also provides a method for treating Alzheimer's disease comprising administering to an individual a therapeutically effective amount of a compound of formula I.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| | Tablet Formulation (Wet Granulation) | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |

-continued

Tablet Formulation (Wet Granulation)

| Item | Ingredients | mg/tablet | | | |
|---|---|---|---|---|---|
| | | 5 mg | 25 mg | 100 mg | 500 mg |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope.

EXAMPLE 1

4-Fluoro-N-(4-methoxy-7-phenyl-benzooxazol-2-yl)-benzamide a) 2-Amino-benzooxazol-4-ol To a stirred solution of 30 g (193 mmol) 2-nitroresorcinol in 900 ml methanol was added 2.00 g 10% palladium on charcoal, and the mixture was then stirred for 18 h at room temperature under an atmosphere of hydrogen. The mixture was then filtered and the filtrate, which contained 2-aminoresorcinol, added dropwise to a stirred solution of 22.5 g (213 mmol) cyanogen bromide in 230 ml methanol and 100 ml water. Stirring was continued for 2 h at room temperature, and then the mixture was concentrated in vacuo. To the residue was added aqueous sodium bicarbonate solution, and the mixture was extracted three times with ethyl acetate. The combined organic phases were washed with saturated brine, dried over sodium sulfate, and concentrated in vacuo. Flash chromatography (ethyl acetate) followed by trituration in ether afforded 27.0 g (93%) 2-amino-benzooxazol-4-ol as a beige crystalline solid. EI-MS m/e (%): 150 (M$^+$, 100), 107 (28).

b) 4-Methoxy-benzooxazol-2-yl-amine

To a stirred solution of 10 g (66 mmol) 2-amino-benzooxazol-4-ol in 100 ml tetrahydrofuran at room temperature was added portionwise 3.49 g (79.9 mmol) sodium hydride (55% dispersion in oil), and the mixture was then stirred for 1 h at 50° C. A solution of 14.5 ml (233 mmol) iodomethane in 500 ml tetrahydrofuran was then added dropwise over 3 h, while the reaction mixture was maintained at 50° C. The mixture was then poured onto water and extracted three times with ethyl acetate. The combined organic phases were washed with saturated brine, dried over sodium sulfate, and concentrated in vacuo. Flash chromatography (dichloromethane then 2/98 methanol/dichloromethane) afforded 7.5 g (69%) 4-methoxy-benzooxazol-2-yl-amine as a brown crystalline solid. EI-MS m/e (%): 164 (M$^+$, 100), 149 ([M−CH$_3$]$^+$, 23), 135 (46).

c) (4-Methoxy-benzooxazol-2-yl)-carbamic acid methyl ester

To a stirred solution of 65 g (40 mmol) 4-methoxy-benzooxazol-2-yl-amine and 4.5 ml (56 mmol) pyridine in 250 ml dichoromethane at 0° C. was added dropwise a solution of 4.1 ml (49 mmol) methyl chloroformate in 50 ml dichoromethane and stirring continued for 3.5 hours. The mixture was then poured onto water and extracted three times with dichloromethane. The combined organic phases were dried over sodium sulfate and concentrated in vacuo. Flash chromatography (dichloromethane) afforded 4.7 g (54%) (4-methoxy-benzooxazol-2-yl)-carbamic acid methyl ester as an off-white crystalline solid. EI-MS m/e (%): 222 (M$^+$, 100), 190 (27), 163 (23).

d) (7-Iodo-4-methoxy-benzooxazol-2-yl)-carbamic acid methyl ester

To a stirred solution of 40 g (18 mmol) (4-methoxy-benzooxazol-2-yl)-carbamic acid methyl ester and 4.4 g (54 mmol) sodium acetate in 20 ml acetic acid at room temperature was added dropwise 8.8 g (54 mmol) iodine monochloride and stirring continued for 30 h. The mixture was then poured onto water and extracted three times with ethyl acetate. The combined organic phases were washed with 1 M aqueous sodium thiosulphate solution, then dried over sodium sulfate and concentrated in vacuo. Trituration in ether afforded 4.1 g (65%) (7-iodo-4-methoxy-benzooxazol-2-yl)-carbamic acid methyl ester as a white crystalline solid. ES-MS m/e (%): 349 (M+H$^+$, 100).

e) 4-Methoxy-7-phenyl-benzooxazol-2-ylamine

To a stirred solution of 820 mg (2.36 mmol) (7-iodo-4-methoxy-benzooxazol-2-yl)-carbamic acid methyl ester in 20 ml N,N-dimethylformamide were added 1.17 ml (3.58 mmol) phenyltri-n-butylstannane, 162 mg (0.18 mmol) tris (dibenzylideneacetone) dipalladium(0), 65 mg (0.21 mmol) triphenylarsine and 208 mg (1.09 mmol) copper(I) iodide. The mixture was heated at 80° C. for 16 h and then poured onto water and extracted three times with ethyl acetate. The combined organic phases were washed with brine, dried over sodium sulfate, and concentrated in vacuo. Flash chromatography (1/99 methanol/dichloromethane) followed by trituration in ether afforded 200 mg 4-methoxy-7-phenyl-benzooxazol-2-yl-amine as a white solid. ES-MS m/e (%): 241 (M+H$^+$, 100).

f) 4-Fluoro-N-(4-methoxy-7-phenyl-benzooxazol-2-yl)-benzamide

To a stirred solution of 100 mg (0.42 mmol) 4-methoxy-7-phenyl-benzooxazol-2-ylamine, 0.087 ml (0.62 mmol) triethylamine and 5.1 mg N,N-dimethyl-4-aminopyridine in 5 ml THF at room temperature was added dropwise a solution of 0.064 ml (0.54 mmol) 4-fluoro-benzoyl chloride in 2 ml THF and stirring continued at 65° C. for 16 h. The reaction mixture was then concentrated in vacuo. To the residue was added water, and the mixture was extracted three times with dichloromethane. The combined organic phases were dried over sodium sulfate and concentrated in vacuo. Flash chromatography (1/4 then 4/1 ethyl acetate/hexane) followed by trituration in ether afforded 50 mg (33%) 4-fluoro-N-(4-methoxy-7-phenyl-benzooxazol-2-yl)-benzamide as a light yellow crystalline solid. EI-MS m/e (%): 362 (M+, 90), 123 ([FC$_6$H$_4$CO+, 100).

In an analogous manner there was obtained:

EXAMPLE 2

4-{[(2-Methoxy-ethyl)-methyl-amino]-methyl}-N-(4-methoxy-7-phenyl-benzooxazol-2-yl)-benzamide From 4-methoxy-7-phenyl-benzooxazol-2-yl-amine with 4-{[(2-methoxy-ethyl)-methyl-amino]-methyl}-benzoyl chloride, triethylamine and N,N-dimethyl-4-aminopyridine in THF. ES-MS m/e (%): 446 (M+H+, 100).

EXAMPLE 3

[7-(3,6-Dihydro-2H-pyran-4-yl)-4-methoxy-benzooxazol-2-yl]-carbamic acid methyl ester To a stirred solution of 350 g (10.1 mmol) (7-iodo-4-methoxy-benzooxazol-2-yl)-carbamic acid methyl ester in 50 ml dioxane were added 5.63 g (15.1 mmol) tributyl-(3,6-dihydro-2H-pyran-4-yl)-stannane, 173 mg (0.30 mmol) bis(dibenzylideneacetone)palladium(0), 374 mg (1.61 mmol) tri(2-furyl)phospine. The mixture was heated at 100° C. for 22 h and then poured onto water and extracted three times with ethyl acetate. The combined organic phases were dried over sodium sulfate and concentrated in vacuo. Flash chromatography (2/98 methanol/dichloromethane then 5/95 methanol/dichloromethane) followed by trituration in dichloromethane afforded 1.30 g (42%) [7-(3,6-dihydro-2H-pyran-4-yl)-4-methoxy-benzooxazol-2-yl]-carbamic acid methyl ester as a white solid. ES-MS m/e (%): 305 (M+H+, 100).

EXAMPLE 4

2-Bromo-N-[4-methoxy-7-(tetrahydro-pyran-4-yl)-benzooxazol-2-yl]-isonicotinamide a) [4-Methoxy-7-(tetrahydro-pyran-4-yl)-benzooxazol-2-yl]-carbamic acid methyl ester To a stirred solution of 130 g (4.27 mmol) [7-(3,6-dihydro-2H-pyran-4-yl)-4-methoxy-benzooxazol-2-yl]-carbamic acid methyl ester in 250 ml methanol and 250 ml dichoromethane was added 1.00 g of 10% palladium on charcoal, and the mixture was then stirred for 10 h at room temperature under an atmosphere of hydrogen. The mixture was then filtered, washing with dichloromethane/methanol (1/1), and the filtrate concentrated in vacuo to afford 1.30 g (100%) [4-methoxy-7-(tetrahydro-pyran-4-yl)-benzooxazol-2-yl]-carbamic acid methyl ester as an off-white solid. ES-MS m/e (%): 307 (M+H+, 100).

b) 4-Methoxy-7-(tetrahydro-pyran-4-yl)-benzooxazol-2-ylamine

To a stirred solution of 130 g (4.24 mmol) [4-methoxy-7-(tetrahydro-pyran-4-yl)-benzooxazol-2-yl]-carbamic acid methyl ester in 90 ml dioxane and 30 ml ethylene glycol was added 90 ml of a 5 N aq. sodium hydroxide solution, and the mixture was heated at 100° C. for 16 h. After cooling to room temperature, the mixture was poured onto water and extracted four times with ethyl acetate. The combined organic phases were dried over sodium sulphate and concentrated in vacuo. Flash chromatography (dichloromethane then 5/95 methanol/dichloromethane) afforded 0.78 g (74%) 4-methoxy-7-(tetrahydro-pyran-4-yl)-benzooxazol-2-ylamine as a brown solid. ES-MS m/e (%): 249 (M+H+, 100).

c) 2-Bromo-N-[4-methoxy-7-(tetrahydro-pyran-4-yl)-benzooxazol-2-yl]-isonicotinamide To a stirred solution of 106 mg (0.52 mmol) 2-bromo-isonicotinic acid in 5 ml THF were added 230 mg (0.60 mmol) HATU and 0.10 ml (0.60 mmol) N-ethyldiisopropylamine and stirring continued at room temperature for 5 h. A solution of 100 mg (0.40 mmol) 4-methoxy-7-(tetrahydro-pyran-4-yl)-benzooxazol-2-ylamine in 5 ml dioxane and 1 ml DMF was then added and stirring continued at 40° C. for 72 h. The reaction mixture was then poured into 100 ml water and extracted three times with ethyl acetate. The combined organic phases were dried over sodium sulfate and concentrated in vacuo. Flash chromatography (dichoromethane then methanol/dichloromethane 20/80) followed by trituration in ether afforded 146 mg (84%) 2-bromo-N-[4-methoxy-7-(tetrahydro-pyran-4-yl)-benzooxazol-2-yl]-isonicotinamide as a white crystalline solid. ES-MS m/e (%): 434 (M{$^{81}$Br}+H+, 95), 432 (M{$^{79}$Br}+H+, 100).

In an analogous manner there were obtained:

EXAMPLE 5

4-Fluoro-N-[4-methoxy-7-(tetrahydro-pyran-4-yl)-benzooxazol-2-yl]-benzamide

From 4-fluorobenzoic acid, HATU and N-diethylisopropylamine in THF, then treatment with 4-methoxy-7-(tetrahydro-pyran-4-yl)-benzooxazol-2-yl-amine in dioxane and DMF. ES-MS m/e (%): 371 (M+H+, 100).

EXAMPLE 6

N-[4-Methoxy-7-(tetrahydro-pyran-4-yl)-benzooxazol-2-yl]-6-methyl-nicotinamide

From 6-methylnicotinic acid, HATU and N-diethylisopropylamine in THF, then treatment with 4-methoxy-7-(tetrahydro-pyran-4-yl)-benzooxazol-2-yl-amine in dioxane and DMF. ES-MS m/e (%): 368 (M+H+, 100).

EXAMPLE 7

N-[4-Methoxy-7-(tetrahydro-pyran-4-yl)-benzooxazol-2-yl]-2-methyl-isonicotinamide From 2-methylisonicotinic acid, HATU and N-diethylisopropylamine in THF, then treatment with 4-methoxy-7-(tetrahydro-pyran-4-yl)-benzooxazol-2-yl-amine in dioxane and DMF. ES-MS m/e (%): 368 (M+H+, 100).

EXAMPLE 8

2-Chloromethyl-N-[4-methoxy-7-(tetrahydro-pyran-4-yl)-benzooxazol-2-yl]-isonicotinamide From 2-chloromethyl-isonicotinic acid, HATU and N-diethylisopropylamine in THF, then treatment with 4-methoxy-7-(tetrahydro-pyran-4-yl)-benzooxazol-2-yl-amine in dioxane and DMF. ES-MS m/e (%): 404 (M{$^{37}$Cl}+H$^+$, 30), 402 (M{$^{35}$Cl}+H$^+$, 100).

EXAMPLE 9

N-[4-Methoxy-7-(tetrahydro-pyran-4-yl)-benzooxazol-2-yl]-2-morpholin-4-yl-isonicotinamide A stirred suspension of 460 mg (1.06 mmol) 2-bromo-N-[4-methoxy-7-(tetrahydro-pyran-4-yl)-benzooxazol-2-yl]-isonicotinamide, 693 mg (2.13 mmol) cesium carbonate and a few crystals of 2,6-di-tert-butyl-p-cresol in 2.78 ml (3.19 mmol) morpholine and 2 ml N-methylpyrrolidone in a thick-walled glass pressure tube fitted with a teflon cap was heated at 140° C. for 24 h. The reaction mixture was then cooled to room temperature and poured onto water. The mixture was extracted three times with ethyl acetate, and the combined organic phases were dried over sodium sulfate and concentrated in vacuo. Flash chromatography (2/98 methanol/dichloromethane) followed by trituration in ether afforded 136 mg (29%) N-[4-methoxy-7-(tetrahydro-pyran-4-yl)-benzooxazol-2-yl]-2-morpholin-4-yl-isonicotinamide as a white crystalline solid. ES-MS m/e (%): 439 (M+H$^+$, 100).

EXAMPLE 10

2-Methoxymethyl-N-[4-methoxy-7-(tetrahydro-pyran-4-yl)-benzooxazol-2-yl]-isonicotinamide To a stirred solution of 0.05 ml (1.24 mmol) methanol in 5 ml dioxane and 1 ml N,N-dimethylformamide at room temperature was added 27 mg (0.62 mmol) sodium hydride (55% dispersion in mineral oil), and the mixture heated at 50° C. for 1 hour. 50 mg (0.12 mmol) 2-chloromethyl-N-[4-methoxy-7-(tetrahydro-pyran-4-yl)-benzooxazol-2-yl]-isonicotinamide was then added, and the mixture heated at 50° C. for 20 h. The reaction mixture was then cooled to room temperature and poured onto water. The mixture was acidified with 1 N aq. hydrochloric acid and then extracted three times with dichloromethane. The combined organic phases were dried over sodium sulfate and concentrated in vacuo. Flash chromatography (dichloromethane) followed by trituration in ether afforded 32 mg (65%) 2-methoxymethyl-N-[4-methoxy-7-(tetrahydro-pyran-4-yl)-benzooxazol-2-yl]-isonicotinamide as a white crystalline solid. ES-MS m/e (%): 398 (M+H$^+$, 100).

Analogously to Example 4 there was obtained:

EXAMPLE 11

N-[4-Methoxy-7-(tetrahydro-pyran-4-yl)-benzooxazol-2-yl]-2-phenyl-acetamide

From phenylacetic acid, HATU and N-diethylisopropylamine in THF, then treatment with 4-methoxy-7-(tetrahydro-pyran-4-yl)-benzooxazol-2-yl-amine in dioxane and DMF. ES-MS m/e (%): 367 (M+H$^+$, 100).

EXAMPLE 12

2-Bromo-N-[7-(4-fluoro-phenyl)-4-methoxy-benzooxazol-2-yl]-isonicotinamide a) [7-(4-Fluoro-phenyl)-4-methoxy-benzooxazol-2-yl]-carbamic acid methyl ester To a stirred solution of 3.00 g (8.62 mmol) (7-iodo-4-methoxy-benzooxazol-2-yl)-carbamic acid methyl ester in 20 ml dioxane and 60 ml 1,2-dimethoxyethane were added 731 mg (17.2 mmol) lithium chloride, 299 mg (0.26 mmol) tetrakis(triphenyl-phosphine)palladium(0), 1.45 g (10.3 mmol) para-fluorobenzeneboronic acid and 18 ml of a 1 N aq. solution of sodium bicarbonate. The mixture was heated at 100° C. for 24 h and then poured onto water and extracted three times with ethyl acetate. The combined organic phases were dried over sodium sulfate and concentrated in vacuo. Trituration in ether afforded 2.67 g (98%) [7-(4-fluoro-phenyl)-4-methoxy-benzooxazol-2-yl]-carbamic acid methyl ester as an off-white solid. ES-MS m/e (%): 317 (M+H$^+$, 100).

b) 7-(4-Fluoro-phenyl)-4-methoxy-benzooxazol-2-ylamine

To a stirred solution of 2.80 g (8.85 mmol) [7-(4-fluoro-phenyl)-4-methoxy-benzooxazol-2-yl]-carbamic acid methyl ester in 100 ml dioxane and 30 ml ethylene glycol was added 100 ml of a 5 N aq. sodium hydroxide solution, and the mixture was heated at 100° C. for 16 h. After cooling to room temperature the mixture was poured onto water and extracted three times with ethyl acetate. The combined organic phases were washed with brine, then dried over sodium sulphate and concentrated in vacuo. Trituration in ether afforded 0.95 g (42%) 7-(4-fluoro-phenyl)-4-methoxy-benzooxazol-2-yl-amine as an off-white solid. ES-MS m/e (%): 259 (M+H$^+$, 100).

c) 2-Bromo-N-[7-(4-fluoro-phenyl)-4-methoxy-benzooxazol-2-yl]-isonicotinamide

To a stirred solution of 203 mg (1.00 mmol) 2-bromo-isonicotinic acid in 5 ml THF were added 442 mg (1.16 mmol) HATU and 0.20 ml (1.16 mmol) N-ethyldiisopropylamine and stirring continued at room temperature for 5 h. A solution of 200 mg (0.77 mmol) 7-(4-fluoro-phenyl)-4-methoxy-benzooxazol-2-yl-amine in 5 ml dioxane and 1 ml DMF was then added and stirring continued at 40° C. for 16 h. The reaction mixture was then poured into 100 ml water and extracted three times with ethyl acetate. The combined organic phases were dried over sodium sulfate and concentrated in vacuo. Trituration in ether/ethyl acetate (4/1) afforded 233 mg (68%) 2-bromo-N-[7-(4-fluoro-phenyl)-4-methoxy-benzooxazol-2-yl]-isonicotinamide as an off-white crystalline solid. ES-MS m/e (%): 444 (M{$^{81}$Br}+H$^+$, 90), 442 (M{$^{79}$Br}+H$^+$, 100).

In an analogous manner there were obtained:

EXAMPLE 13

2-Chloromethyl-N-[7-(4-fluoro-phenyl)-4-methoxy-benzooxazol-2-yl]-isonicotinamide From 2-chloromethyl-isonicotinic acid, HATU and N-diethylisopropylamine in THF, then treatment with 7-(4-fluoro-phenyl)-4-methoxy-benzooxazol-2-yl-amine in dioxane and DMF. ES-MS m/e (%): 414 (M{$^{37}$Cl}+H$^+$, 30), 412 (M{$^{35}$Cl}+H$^+$, 100).

EXAMPLE 14

N-[7-(4-Fluoro-phenyl)-4-methoxy-benzooxazol-2-yl]-2-methyl-isonicotinamide

From 2-methyl-isonicotinic acid, HATU and N-diethylisopropylamine in THF, then treatment with 7-(4-fluoro-phenyl)-4-methoxy-benzooxazol-2-yl-amine in dioxane and DMF. ES-MS m/e (%): 378 (M+H$^+$, 100).

EXAMPLE 15

N-[7-(4-Fluoro-phenyl)-4-methoxy-benzooxazol-2-yl]-propionamide

From propionic acid, HATU and N-diethylisopropylamine in THF, then treatment with 7-(4-fluoro-phenyl)-4-methoxy-benzooxazol-2-ylamine in dioxane and DMF. ES-MS m/e (%): 315 (M+H$^+$, 100).

EXAMPLE 16

N-[7-(4-Fluoro-phenyl)-4-methoxy-benzooxazol-2-yl]-2-methoxy-acetamide

From methoxyacetic acid, HATU and N-diethylisopropylamine in THF, then treatment with 7-(4-fluoro-phenyl)-4-methoxy-benzooxazol-2-yl-amine in dioxane and DMF. ES-MS m/e (%): 331 (M+H$^+$, 100).

EXAMPLE 17

N-[7-(4-Fluoro-phenyl)-4-methoxy-benzooxazol-2-yl]-6-methyl-nicotinamide

From 6-methyl-nicotinic acid, HATU and N-diethylisopropylamine in THF, then treatment with 7-(4-fluoro-phenyl)-4-methoxy-benzooxazol-2-yl-amine in dioxane and DMF. ES-MS m/e (%): 378 (M+H$^+$, 100).

EXAMPLE 18

4-Fluoro-N-[7-(4-fluoro-phenyl)-4-methoxy-benzooxazol-2-yl]-benzamide

From 4-fluorobenzoic acid, HATU and N-diethylisopropylamine in THF, then treatment with 7-(4-fluoro-phenyl)-4-methoxy-benzooxazol-2-yl-amine in dioxane and DMF. ES-MS m/e (%): 381 (M+H$^+$, 100).

EXAMPLE 19

N-[7-(4-Fluoro-phenyl)-4-methoxy-benzooxazol-2-yl]-2-phenyl-acetamide

From phenylacetic acid, HATU and N-diethylisopropylamine in THF, then treatment with 7-(4-fluoro-phenyl)-4-methoxy-benzooxazol-2-yl-amine in dioxane and DMF. ES-MS m/e (%): 377 (M+H$^+$, 100).

Analogously to example 9 there was obtained:

EXAMPLE 20

N-[7-(4-Fluoro-phenyl)-4-methoxy-benzooxazol-2-yl]-2-morpholin-4-yl-isonicotinamide From 2-bromo-N-[7-(4-fluoro-phenyl)-4-methoxy-benzooxazol-2-yl]-isonicotinamide with cesium carbonate and morpholine in NMP. ES-MS m/e (%): 449 (M+H$^+$, 100).

Analogously to example 10 there was obtained:

EXAMPLE 21

N-[7-(4-Fluoro-phenyl)-4-methoxy-benzooxazol-2-yl]-2-methoxymethyl-isonicotinamide From 2-chloromethyl-N-[7-(4-fluoro-phenyl)-4-methoxy-benzooxazol-2-yl]-isonicotinamide with sodium hydride and ethanol in dioxane and DMF. ES-MS m/e (%): 408 (M+H$^+$, 100).

EXAMPLE 22

2-Chloromethyl-N-(4-methoxy-7-morpholin-4-yl-benzooxazol-2-yl)-isonicotinamide a) (4-Methoxy-7-nitro-benzooxazol-2-yl)-carbamic acid methyl ester To a stirred solution of 780 mg (3.51 mmol) (4-methoxy-benzooxazol-2-yl)-carbamic acid methyl ester in 40 ml nitromethane at 0° C. was added 699 mg (5.27 mmol) nitronium tetrafluoroborate and stirring continued for 18 h while the reaction mixture was allowed to warm gradually to room temperature. The mixture was then concentrated in vacuo. Flash chromatography (ethyl acetate/hexane) afforded 300 mg (32%) (4-methoxy-5-nitro-benzooxazol-2-yl)-carbamic acid methyl ester as an orange solid, and 220 mg (32%) (4-methoxy-7-nitro-benzooxazol-2-yl)-carbamic acid methyl ester as a yellow solid. ES-MS m/e (%): 268 (M+H$^+$, 100).

b) (7-Amino-4-methoxy-benzooxazol-2-yl)-carbamic acid methyl ester

To a stirred solution of 220 mg (0.82 mmol) (4-methoxy-7-nitro-benzooxazol-2-yl)-carbamic acid methyl ester in 25 ml methanol and 45 ml dichloromethane was added a spatula end of 10% palladium on charcoal and stirring continued for 18 h at room temperature under an atmosphere of hydrogen. The mixture was then filtered and the filtrate concentrated in vacuo. Flash chromatography (2/98 methanol/dichloromethane) afforded 114 mg (58%) (7-amino-4-methoxy-benzooxazol-2-yl)-carbamic acid methyl ester as a white crystalline solid. ES-MS m/e (%): 238 (M+H$^+$, 100).

c) 4-Methoxy-benzooxazole-2,7-diamine

To a stirred solution of 100 mg (0.42 mmol) (7-amino-4-methoxy-benzooxazol-2-yl)-carbamic acid methyl ester in 15 ml dioxane and 5 ml ethylene glycol was added 15 ml of a 5 N aq. sodium hydroxide solution and the mixture was heated at 100° C. for 4 h. After cooling to room temperature the mixture was poured onto water and extracted three times with ethyl acetate. The combined organic phases were dried over sodium sulphate and concentrated in vacuo. Flash chromatography (5/95 methanol/dichloromethane, then 10/89/1 methanol/dichloromethane/triethylamine) followed by trituration in ether afforded 15 mg (20%) 4-methoxy-benzooxazole-2,7-diamine as a brown solid. ES-MS m/e (%): 180 (M+H$^+$, 100).

d) 4-Methoxy-7-morpholin-4-yl-benzooxazol-2-yl-amine

To a stirred solution of 800 mg (4.47 mmol) 4-methoxy-benzooxazole-2,7-diamine in 40 ml DMF at room temperature were added 2.47 g (17.9 mmol) potassium carbonate and 2.18 g (6.70 mmol) 1-iodo-2-(2-iodo-ethoxy)-ethane and the mixture heated at 60° C. for 48 h. After cooling to room temperature the mixture was poured onto water and extracted three times with ethyl acetate. The combined organic phases were washed with brine, then dried over sodium sulphate and concentrated in vacuo. Flash chromatography (2/98 methanol/dichloromethane, then 10/90 methanol/dichloromethane) afforded 585 mg (53%) 4-methoxy-7-morpholin-4-yl-benzooxazol-2-ylamine as a light brown solid. ES-MS m/e (%): 250 (M+H$^+$, 100).

e) 2-Chloromethyl-N-(4-methoxy-7-morpholin-4-yl-benzooxazol-2-yl)-isonicotinamide To a stirred solution of 72 mg (0.42 mmol) 2-choromethyl-isonicotinic acid in 5 ml THF were added 183 mg (0.48 mmol) HATU and 0.08 ml (0.48 mmol) N-ethyldiisopropylamine and stirring continued at room temperature for 5 h. A solution of 80 mg (0.32 mmol) 4-methoxy-7-morpholin-4-yl-benzooxazol-2-yl-amine in 5 ml dioxane and 1 ml DMF was then added and stirring continued at 40° C. for 48 h. The reaction mixture was then poured into 50 ml water, acidified with 1 M aq. hydrochloric acid, and extracted three times with ethyl acetate. The combined organic phases were dried over sodium sulfate and concentrated in vacuo. Flash chromatography (3/97 methanol/dichloromethane, then 10/90 methanol/dichloromethane) followed by trituration in ether afforded 8 mg (6%) 2-chloromethyl-N-(4-methoxy-7-morpholin-4-yl-benzooxazol-2-yl)-isonicotinamide as an off-white crystalline solid. ES-MS m/e (%): 405 (M{$^{37}$Cl}+H$^+$, 35), 403 (M{$^{35}$Cl}+H$^+$, 100).

In an analogous manner there were obtained:

EXAMPLE 23

N-(4-Methoxy-7-morpholin-4-yl-benzooxazol-2-yl)-6-methyl-nicotinamide

From 6-methyl-nicotinic acid, HATU and N-diethylisopropylamine in THF, then treatment with 4-methoxy-7-morpholin-4-yl-benzooxazol-2-yl-amine in dioxane and DMF. ES-MS m/e (%): 369 (M+H$^+$, 100).

EXAMPLE 24

4-Fluoro-N-(4-methoxy-7-morpholin-4-yl-benzooxazol-2-yl)-benzamide

From 4-fluorobenzoic acid, HATU and N-diethylisopropylamine in THF, then treatment with 4-methoxy-7-morpholin-4-yl-benzooxazol-2-ylamine in dioxane and DMF. ES-MS m/e (%): 372 (M+H$^+$, 100).

Analogously to Example 9 there was obtained:

EXAMPLE 25

N-(4-Methoxy-7-morpholin-4-yl-benzooxazol-2-yl)-2-morpholin-4-yl-isonicotinamide From 2-bromo-isonicotinic, HATU and N-diethylisopropylamine in THF, followed by treatment with 4-methoxy-7-morpholin-4-yl-benzooxazol-2-yl-amine in dioxane. Then treatment with cesium carbonate and morpholine in NMP. ES-MS m/e (%): 440 (M+H$^+$, 100).

EXAMPLE 26

N-[7-(4-Fluoro-phenyl)-4-methoxy-benzooxazol-2-yl]-2-pyrrolidin-1-ylmethyl-isonicotinamide A mixture of 100 mg (0.24 mmol) 2-chloromethyl-N-[7-(4-fluoro-phenyl)-4-methoxy-benzooxazol-2-yl]-isonicotinamide and 0.35 g (4.86 mmol) pyrrolidine was ultrasonicated at room temperature for 10 minutes. The reaction mixture was then poured into water and extracted three times with ethyl acetate. The combined organic phases were dried over sodium sulfate and concentrated in vacuo. Trituration in ether/ethyl acetate (5/1) afforded 56 mg (52%) N-[7-(4-fluoro-phenyl)-4-methoxy-benzooxazol-2-yl]-2-pyrrolidin-1-ylmethyl-isonicotinamide as a yellow crystalline solid. ES-MS m/e (%): 447 (M+H$^+$, 100).

In an analogous manner was obtained:

EXAMPLE 27

N-[7-(4-Fluoro-phenyl)-4-methoxy-benzooxazol-2-yl]-2-morpholin-4-yl-methyl-isonicotinamide From 2-chloromethyl-N-[7-(4-fluoro-phenyl)-4-methoxy-benzooxazol-2-yl]-isonicotinamide and morpholine. ES-MS m/e (%): 463 (M+H$^+$, 100).

What is claimed is:
1. A compound of formula

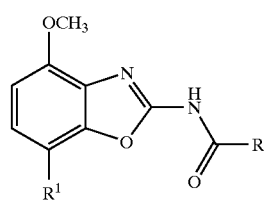

I wherein
R is phenyl, unsubstituted or substituted by halogen or —CH$_2$N(CH$_3$)(CH$_2$)$_n$OCH$_3$, or
is benzyl,
lower alkyl,
lower alkoxy,
—(CH$_2$)$_n$OCH$_3$, or is
pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl;
R$^1$ is phenyl, unsubstituted or substituted by halogen, tetrahydropyran-4-yl, 3,6-dihydro-2H-pyran-4-yl or morpholin-4-yl;
n is independently from each other 1 or 2;
and pharmaceutically acceptable acid addition salts thereof.

2. A compound of formula I in accordance with claim 1, wherein R$^1$ is 4-fluoro phenyl.

3. A compound of formula I in accordance with claim 2, selected from the group consisting of
2-Chloromethyl-N-[7-(4-fluoro-phenyl)-4-methoxy-benzooxazol-2-yl]-isonicotinamide,
N-[7-(4-fluoro-phenyl)-4-methoxy-benzooxazol-2-yl]-2-methyl-isonicotinamide,
N-[7-(4-fluoro-phenyl)-4-methoxy-benzooxazol-2-yl]-6-methyl-nicotinamide
4-fluoro-N-[7-(4-fluoro-phenyl)-4-methoxy-benzooxazol-2-yl]-benzamide,
N-[7-(4-fluoro-phenyl)-4-methoxy-benzooxazol-2-yl]-2-morpholin-4-yl-isonicotinamide and
N-[7-(4-fluoro-phenyl)-4-methoxy-benzooxazol-2-yl]-2-methoxymethyl-isonicotinamide.

4. A compound of formula I in accordance with claim 2, wherein R is selected from phenyl, unsubstituted or substituted by halogen or —CH$_2$N(CH$_3$)(CH$_2$)OCH$_3$, and benzyl.

5. A compound of formula I in accordance with claim 2, wherein R is selected from lower alkyl, lower alkoxy, and —(CH$_2$)$_n$OCH$_3$, and n is independently from each other 1 or 2.

6. A compound of formula I in accordance with claim 2, wherein R is pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl.

7. A compound of formula I in accordance with claim 1, wherein R$^1$ is unsubstituted phenyl.

8. A compound of formula I in accordance with claim 7, selected from the group consisting of
4-fluoro-N-(4-methoxy-7-phenyl-benzooxazol-2-yl)-benzamide and
4-{[(2-methoxy-ethyl)-methyl-amino]-methyl}-N-(4-methoxy-7-phenyl-benzooxazol-2-yl)-benzamide.

9. A compound of formula I in accordance with claim 7, wherein R is selected from phenyl, unsubstituted or substituted by halogen or —CH$_2$N(CH$_3$)(CH$_2$)OCH$_3$, and benzyl.

10. A compound of formula I in accordance with claim 7, wherein R is selected from lower alkyl, lower alkoxy, and —(CH$_2$)$_n$OCH$_3$, and n is independently from each other 1 or 2.

11. A compound of formula I in accordance with claim 7, wherein R is pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl.

12. A compound of formula I in accordance with claim 1, wherein R$^1$ is tetrahydropyran-4-yl.

13. A compound of formula I in accordance with claim 12, selected from the group consisting of
N-[4-Methoxy-7-(tetrahydro-pyran-4-yl)-benzooxazol-2-yl]-6-methyl-nicotinamide and
N-[4-methoxy-7-(tetrahydro-pyran-4-yl)-benzooxazol-2-yl]-2-methyl-isonicotinamide.

14. A compound of formula I in accordance with claim 12, wherein R is selected from phenyl, unsubstituted or substituted by halogen or —CH$_2$N(CH$_3$)(CH$_2$)OCH$_3$, and benzyl.

15. A compound of formula I in accordance with claim 12, wherein R is selected from lower alkyl, lower alkoxy, and —(CH$_2$)$_n$OCH$_3$, and n is independently from each other 1 or 2.

16. A compound of formula I in accordance with claim 12, wherein R is pyridin 3- or 4-yl, unsubstituted or substituted by lower alkyl, halogen, morpholinyl, —(CH$_2$)$_n$-halogen, —(CH$_2$)$_n$OCH$_3$, —(CH$_2$)$_n$-morpholin-4-yl, or —(CH$_2$)$_n$-pyrrolidin-1-yl.

17. A composition comprising a compound of formula I, as defined in claim 1, or a pharmaceutically acceptable salt thereof and a pharmaceutically acceptable carrier.

18. A method of treating Parkinson's disease comprising administering to an individual a therapeutically effective amount of a compound of formula I or a pharmaceutically acceptable salt thereof.

19. A method of treating Alzheimer's disease comprising administering to an individual a therapeutically effective amount of a compound of formula I or a pharmaceutically acceptable salt thereof.

20. A process for preparing a compound of formula I as defined in claim 1, which comprises
reacting a compound of formula

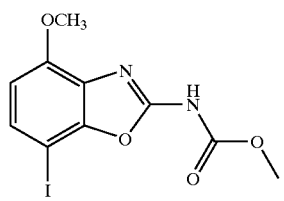

(6)

with a compound of formula

R$^1$SnBu$_3$/cat. Pd(O)  (7) or with a compound of formula

R$^1$B(OH)$_2$/cat. Pd(O)  (10)

to a compound of formula

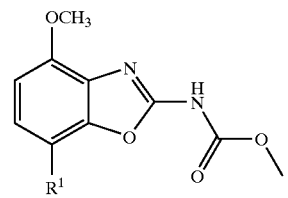

I(8)

wherein R$^1$ is phenyl, unsubstituted or substituted by halogen.

21. A process for preparing a compound of formula I as defined in claim 1 which comprises
reacting a compound of formula

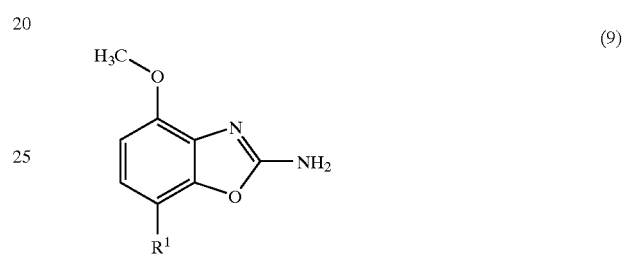

(9)

with a compound of formula

ClC(O)R/base  (11)

or with a compound of formula

HOC(O)R/HATU/base  (12)

to a compound of formula

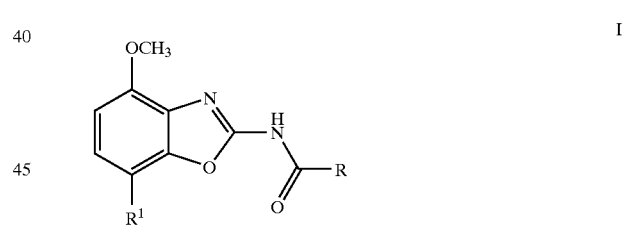

I wherein R$^1$ is unsubstituted phenyl or substituted by halogen.

22. A process for preparing a compound of formula I as defined in claim 1 which comprises
hydrogenating a compound of formula

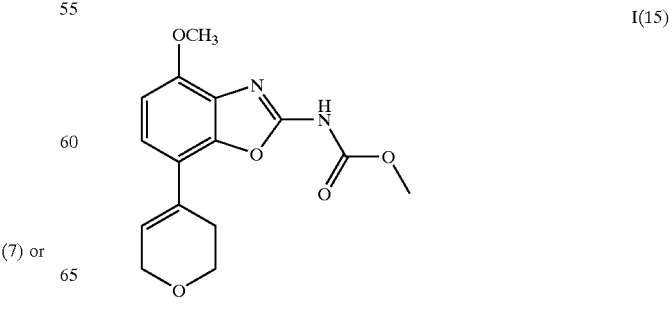

I(15)

with H$_2$/Pd/C to a compound of formula

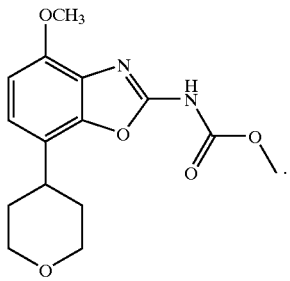

I(16)

23. A process for preparing a compound of formula I as defined in claim 1 which comprises
reacting a compound of formula

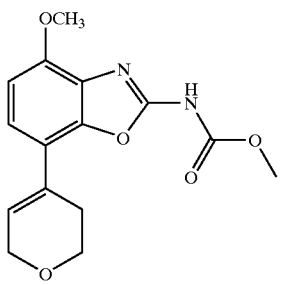

I(15)

with NaOH and then with a compound of formula

ClC(O)R/base  (11)

or with a compound of formula

HOC(O)R/HATU/base  (12)

to a compound of formula

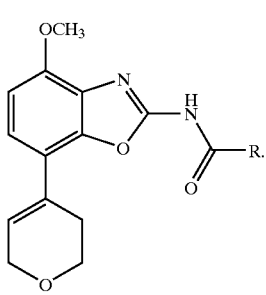

Ia

24. A process for preparing a compound of formula I as defined in claim 1 which comprises
reacting a compound of formula

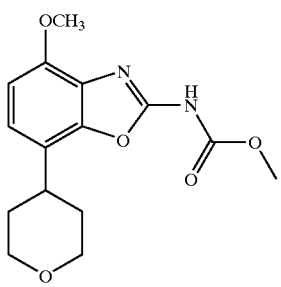

I(16)

with NaOH and then with a compound of formula

ClC(O)R/base  (11)

or with a compound of formula

HOC(O)R/HATU/base  (12)

to a compound of formula

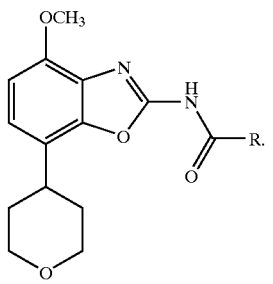

Ib

25. A process for preparing a compound of formula I as defined in claim 1 which comprises
reacting a compound of formula

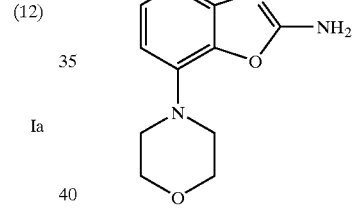

(20)

with a compound of formula

ClC(O)R/base  (11)

or with a compound of formula

HOC(O)R/HATU/base  (12)

to a compound of formula

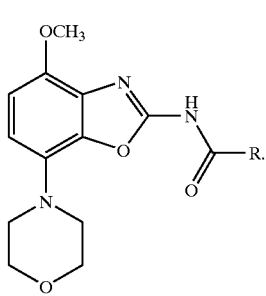

Ic

* * * * *

UNITED STATES PATENT AND TRADEMARK OFFICE
CERTIFICATE OF CORRECTION

PATENT NO. : 6,992,083 B2
APPLICATION NO. : 10/755105
DATED : January 31, 2006
INVENTOR(S) : Roger David Norcross It is certified that error appears in the above-identified patent and that said Letters Patent is hereby corrected as shown below:

TITLE PAGE:

• The Assignee information reads "Hoffman-La Roche Inc., Nutley, NJ (US)".
The Assignee information should read --- Hoffmann-La Roche Inc., Nutley, NJ (US) ---.

Signed and Sealed this

Twenty-ninth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,992,083 B2
APPLICATION NO. : 10/755105
DATED : January 31, 2006
INVENTOR(S) : Roger David Norcross It is certified that error appears in the above-identified patent and that said Letters Patent is hereby corrected as shown below:

TITLE PAGE:

• The patent term adjustment information reads "Notice: Subject to any disclaimer, the term of this patent is extended or adjusted under 35 U.S.C. 154 (b) by 0 days." The patent term adjustment information should read -- Notice: Subject to any disclaimer, the term of this patent is extended or adjusted under 35 U.S.C. 154(b) by 35 days. --

Signed and Sealed this

Thirteenth Day of January, 2009

JON W. DUDAS
*Director of the United States Patent and Trademark Office*